United States Patent [19]

Burkholder et al.

[11] Patent Number: 4,592,746
[45] Date of Patent: Jun. 3, 1986

[54] SYRINGE AND LOCKING DEVICE AND METHOD OF ASSEMBLING SAME

[75] Inventors: Richard A. Burkholder, St. Charles; Richard W. Gilson, St. Louis; Clarence L. Walker, Webster Groves, all of Mo.

[73] Assignee: Sherwood Medical Company, St. Louis, Mo.

[21] Appl. No.: 743,126

[22] Filed: Jun. 10, 1985

[51] Int. Cl.⁴ .......................................... A61M 5/315
[52] U.S. Cl. ..................................................... 604/220
[58] Field of Search ............... 604/220, 207, 208, 209, 604/210, 211, 228

[56] References Cited

U.S. PATENT DOCUMENTS

| | | | |
|---|---|---|---|
| 3,938,505 | 2/1976 | Jamshidi | 128/2 B |
| 4,153,056 | 5/1979 | Silver et al. | 604/211 |
| 4,312,343 | 1/1982 | LeVeen et al. | 604/211 |
| 4,386,606 | 6/1983 | Tretinyak et al. | 604/220 |

FOREIGN PATENT DOCUMENTS 2810370 9/1979 Fed. Rep. of Germany ...... 604/208

Primary Examiner—John D. Yasko
Attorney, Agent, or Firm—Stanley N. Garber; Andrew J. Beck; William R. O'Meara

[57] ABSTRACT

A device for selectively locking a syringe plunger against longitudinal movement with respect to the syringe barrel includes two interlocking device parts. Each device part has a generally flat body with a generally semi-circular inner perimeter and first and second ends. A ridge extends along the inner perimeter of each half for engaging the syringe plunger when the plunger is rotated to a predetermined angular position. Each interlocking part has mating structures at each end for mating with the other device part and has a flange for retaining the assembled locking device on the syringe barrel. The syringe and locking device are assembled by inserting the plunger in the syringe barrel and then snapping the two device parts together around the proximal end of the syringe barrel.

7 Claims, 9 Drawing Figures

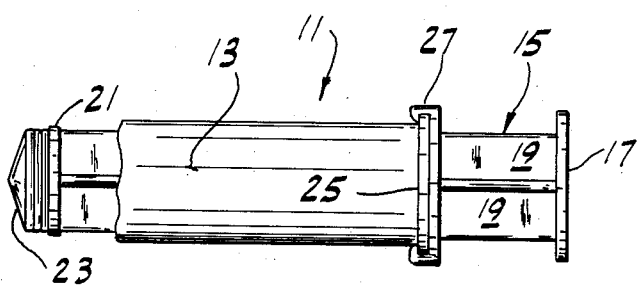
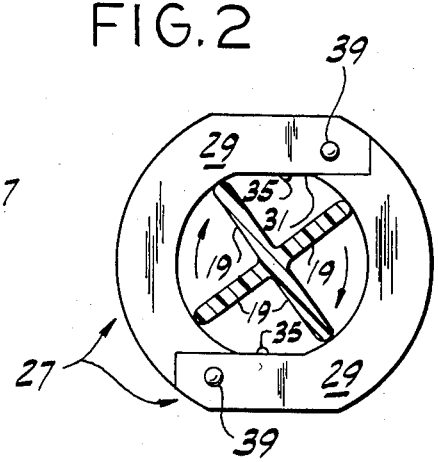
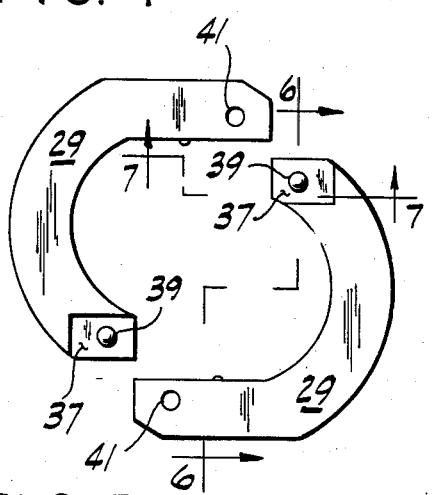
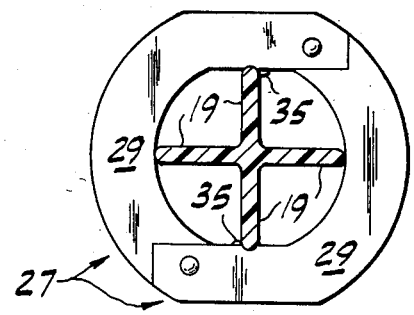
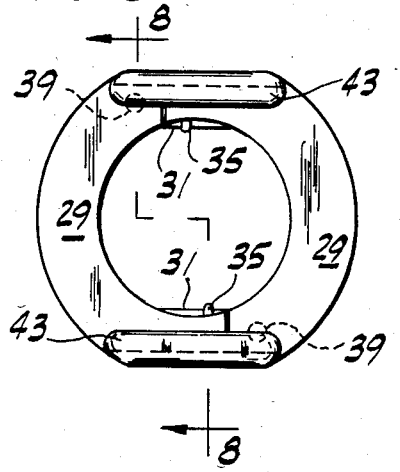
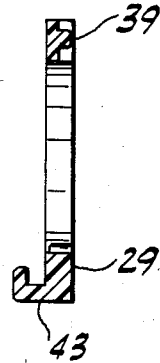
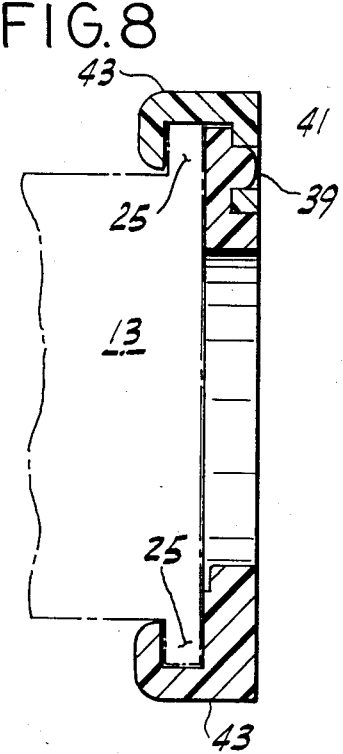

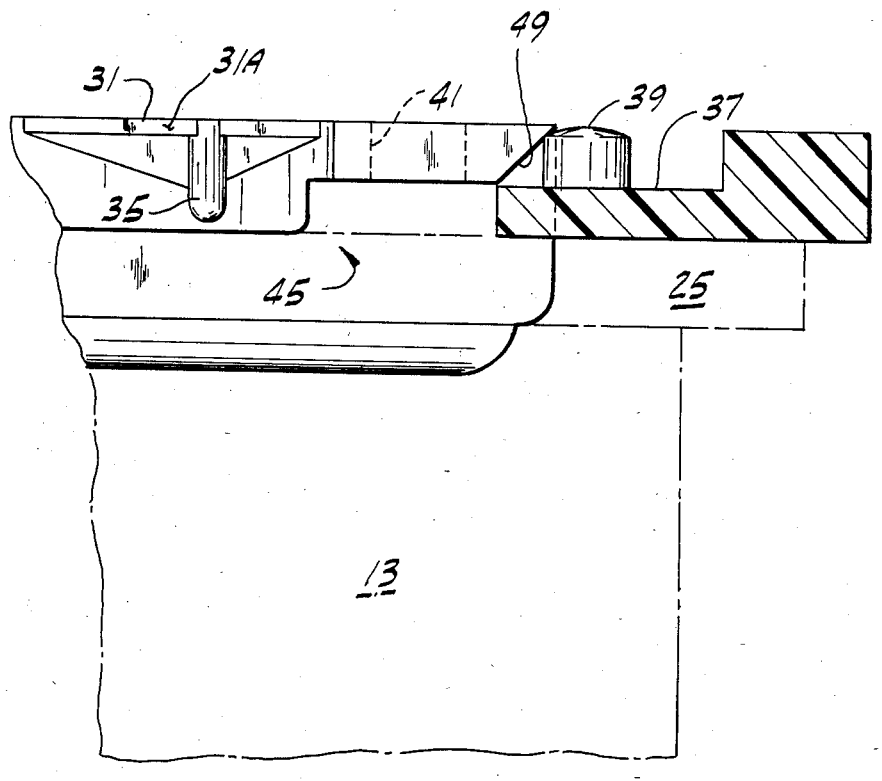
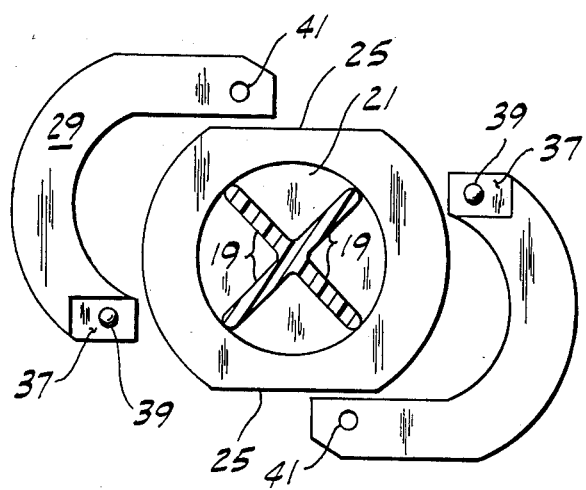

SYRINGE AND LOCKING DEVICE AND METHOD OF ASSEMBLING SAME

BACKGROUND OF THE INVENTION

This invention relates to medical devices and more particularly to syringes with a device for locking the plunger in place with respect to the barrel of the syringe of the type disclosed in applicants' assignee's copending application by Ewalt et al., Ser. No. 06/743,127 filed on June 10, 1985 entitled "Syringe Locking Device".

There are several devices known for restraining a syringe plunger in an extended position while a vacuum is held in the syringe barrel in front of the plunger piston. Such devices might include stepped stops on the plunger such as are shown in U.S. Pat. Nos. 3,882,849 and 3,938,505. These devices, however, require that the standard plunger and/or syringe barrel be modified in some way to provide the locking mechanism. Other devices, such as that shown in U.S. Pat. No. 4,386,606, require a separate moving part to accomplish the desired function. Such moving parts may be relatively difficult to manufacture and to use, and may be less reliable than a device without such an additional moving part.

All these devices would seem to necessitate fairly major changes in the syringe manufacturing process and would possibly add significantly to the cost of a syringe.

SUMMARY OF THE INVENTION

Among the aspects and features of the present invention is the provision of a locking device for a syringe which is usable with standard syringe components; the provision of such a device which involves only relatively minor modifications to the syringe manufacturing process; the provision of such a device which leads to generally error-free assembly; the provision of such a device which is relatively inexpensive; and the provision of such a device which is reliable in operation.

Briefly, in one embodiment the device of the present invention includes two identical interlocking device halves. Each device half has a generally flat body with a generally semi-circular inner perimeter and first and second ends. A ridge is disposed along the inner perimeter of each device half for engaging a syringe plunger. The device halves mate together at each end, and a lip is provided on each for retaining the assembled device on a syringe barrel.

In a second aspect, the present invention includes a syringe barrel having a finger grip at its proximal end and a syringe plunger reciprocally movable in the barrel and having ribs extending transversely out from the longitudinal axis of the plunger. A locking device disposed at the proximal end of the syringe barrel includes a pair of identical, interlocking device halves. Each device half has a generally flat body with a generally semi-circular inner perimeter and first and second ends. A ridge is disposed along the inner perimeter of each device half for engaging the ribs of the syringe plunger upon rotation of the plunger to a predetermined angular position. The device halves mate together at each end, and a lip is provided on each for retaining the assembled device on a syringe barrel.

The method of the present invention of assembling a syringe having a syringe barrel, a syringe plunger and a locking device includes the steps of first inserting the plunger into the syringe barrel and then securing the locking device to the exterior of the syringe barrel at the proximal end thereof, such that the locking device when so secured encircles the syringe plunger.

Other aspects and features will be in part apparent and in part pointed out hereinafter.

BRIEF DESCRIPTION OF THE DRAWINGS

FIG. 1 is a side elevation of the syringe and locking device of the present invention;

FIG. 2 is a front elevation, with parts broken away for clarity, showing the syringe in the unlocked position;

FIG. 3 is a front elevation, similar to FIG. 2, but showing the syringe in the locked position;

FIG. 4 is a front elevation of the locking device of the present invention with the two identical locking device halves separated;

FIG. 5 is a rear elevation of the assembled locking device of the present invention;

FIG. 6 is a section taken along line 6—6 of FIG. 4;

FIG. 7 is a partial view on an enlarged scale, taken along lines 7—7 of FIG. 4 of portions of the locking device halves;

FIG. 8 is a section taken along line 8—8 of FIG. 5; and

FIG. 9 is an enlarged view illustrating the assembly of two locking device halves about a syringe.

Similar reference characters indicate similar parts throughout the several views of the drawings.

DESCRIPTION OF THE PREFERRED EMBODIMENT

Turning now to the drawings, a syringe 11 of the present invention includes a syringe barrel 13 in which a syringe plunger 15 is mounted for longitudinal reciprocation. Plunger 15 includes a thumb rest 17 at its proximal end and four ribs 19 extending at right angles to their neighbors and to the longitudinal axis of the plunger. Plunger 15 terminates at its distal end in a disk 21 to which is secured a piston tip 23 of rubber or simiar material. Syringe barrel 13 and plunger 15 are preferably molded from a suitable plastic such as polypropylene, plunger 15 being molded in a single piece. Syringe barrel 13 terminates at its proximal end in an integrally molded finger grip 25 about which is disposed locking device 27 of the present invention. Locking device 27 is preferably molded from a material such as that sold by Du Pont under the trade designation Rynite which is somewhat harder than polypropylene. For example, the polypropylene used in molding the plunger has a hardness on the Rockwell scale of R95-100 and the Rynite a hardness of R120.

Locking device 27 (see FIG. 2) consists of two identical device halves 29 which interlock with each other to form device 27. Although the halves are shown as identical, it should be appreciated that non-identical mating or interlocking parts could also be used. Each device half has a generally semi-circular inner perimeter and a ridge 31 extending chordally across the inner perimeter constituting means for engaging ribs 19 of plunger 15 when locking is desired. When assembled, the two device halves define the generally circular inner opening shown in FIGS. 2 and 3, which opening has a diameter at least as large as the width of plunger 15 as measured along either opposed pair of ribs 19. As a result, the plunger shaft can be easily moved longitudinally in the syringe barrel to draw any of the range of desired partial vacuums in the barrel. Once the desired partial vaccum is drawn, the plunger is rotated in the direction indicated by the arrows in FIG. 2 until it reaches the locked position shown in FIG. 3. The distance between the chordally extending ridges of the two device halves is less than the width of the plunger as measured along opposed ribs 19, so the plunger is held in place against longitudinal movement by the ridges in the FIG. 3 position, which locks the syringe. This allows the desired partial vacuum to be held in the syringe barrel without the necessity of holding both the barrel and the plunger (which is a two-handed operation). The material of the locking device is preferably harder than the material of the plunger ribs, as described above, because this allows the locking device to more securely hold the plunger in place by actually cutting into the ribs or indenting them. Of course, the plunger need not be rotated fully to the position shown in FIG. 3 to be locked. Ridges 31 in some applications can hold the plunger in place even with a lesser rotation.

A stop 35 is provided on each device half to ensure that the plunger shaft is not accidentally rotated past the position shown in FIG. 3 to another unlocked position. The precise size, placement, and shape of stop 35 is not critical. It is merely desired that it provide a positive stopping action in the locked position and that it be easily moldable as an integral part of locking device half 29.

Although the body of locking device 27 is generally flat (see FIG. 1) with a flat upper surface, each device half has a mating recess 37 (see FIG. 4) in which is disposed a post or male member 39 which extends perpendicularly out from the surface of the recess but which terminates before the flat upper surface of the device itself. The opposite end of each device half 29 includes a female member or opening 41 sized to receive post 39, post 39 terminating within opening 41. Of course, methods of engagement other than a post and hole could be used to lock together the two device halves.

Each locking device half 29 (see FIG. 5) includes an ear 43 disposed generally at the same end of the device half as the chordal ridge and parallel thereto for retaining the locking device on the syringe barrel. More specifically, each ear extends distally from the flat upper surface of the locking device around at least a portion of the finger grip of the syringe barrel (see FIG. 8). In addition to showing the exact shape of ear 43, FIG. 6 also more clearly reveals that post 39 terminates at or below the upper surface of the locking device, so that the flat upper surface of the assembled device is not interrupted.

Ridge 31 (see FIG. 7) of each locking device half has a relatively narrow upper surface 31A suitable for cutting into or indenting the plunger rubs. Ridge 31 widens as it moves away from the central opening. Stop 35 is molded integrally with the ridge but may extend out therefrom for the reasons set forth above. The distal side of device half 29 is notched out as indicated at 45 in the vicinity of opening 41 to provide room for the mating surface 47 of the other device half without increasing the overall width of the device half. The body of the device half includes a ramp 49 leading to notch 45 for reasons which will become apparent.

As noted above, the distance between the ridges of the two assembled device halves is less than the maximum width of the plunger as measured along opposed ribs. That distance could also be slightly less than the diameter of disk 21 at the distal end of the plunger, which creates difficulty in assembling the syringe and locking device combination if the locking device is secured to the syringe barrel before the plunger is inserted into the barrel. Therefore, it is preferred to assemble the syringe and locking device combination by first inserting the plunger into the syringe barrel at least until disk 21 is past the proximal end of the barrel and then securing the locking device to the exterior of the syringe barrel at the proximal end thereof, such that the locking device when so secured encircles the syringe plunger. More specifically, both device halves are placed generally in place as shown in FIG. 9, with the ear 43 of each device half disposed in position about its corresponding finger grip and the post of each abutting the corresponding ramp 49 of the other device half. Then, pressure applied to the outside of each device half to force them together causes each ramp 49 to ride up over corresponding post 39 until the posts snap into openings 41. In this position (see FIG. 8) the device halves hold each other in place at the proximal end of the syringe barrel with the ears of the locking device secured about the finger grip of the syringe barrel.

In view of the above, it will be seen that the various aspects and features of the invention are achieved and other advantageous results attained.

While a preferred embodiment of the present invention has been described, it should be understood that various changes, adaptations, and modifications may be made therein without departing from the spirit of the invention and the scope of the appended claims.

What is claimed is:

1. In a locking device for attachment to the exterior of a syringe barrel, comprising:
    a generally flat body;
    means adapted to fit exteriorly of the syringe barrel for holding the device against rotation when in use on a syringe barrel;
    a generally circular opening in the body for passage of a syringe plunger reciprocatably therethrough;
    at least two ridges extending chordally across the generally circular opening, said ridges being spaced from each other a distance less than the diameter of the generally circular opening and said ridges having a thickness that is less than the thickness of the body; and
    the improvement wherein said body is constructed of two discrete, identical and separate halves adapted to be fixedly connected to each other and to the exterior of the syringe barrel.

2. In a syringe comprising a syringe barrel having a bore therein and distal and proximal ends, said barrel having laterally projecting portions on opposite lateral sides thereof adjacent said proximal end, a syringe plunger locking device fixed to said projecting portions and including locking means projecting into said bore at said proximal end of said barrel, a syring plunger axially slidably and rotatably disposed in said barrel bore, said plunger having a longitudinal axis and radial projecting means fixedly projecting radially and on opposite sides of said longitudinal axis, said plunger being rotatable from a first position wherein said plunger is axially movable in said bore to a second position wherein said projecting means contacts said locking means to thereby axially lock said plunger to said locking device and to said barrel,
    the improvement wherein said locking device comprises discrete and separate first and second locking device halves, each of said halves having a generally semi-circular inner periphery and first and second ends, each of said ends of said halves having a male or a female connector adapted to receive a female or male connector on the other locking device half, each of said halves having retaining means fixed thereto for retaining said half on the laterally projecting portions on one lateral side of the barrel to fix said locking device to the barrel, each of said halves further including said locking means between said first and second ends, said locking means projecting into said bore and extending chordally of said generally semi-circular inner periphery.

3. In a syringe according to claim 2 wherein said first and second locking device halves are identical to each other.

4. In a syringe according to claim 3 wherein said male connectors terminate within said female connector's.

5. In a syringe according to claim 4 wherein each of said locking means includes stop means for preventing rotation of the plunger past a predetermined angular position.

6. In a syringe according to claim 5 wherein said locking means comprising first and second ridges on said first and second locking device halves, respectively, each of said ridges extending chordally across said inner peripheries adjacent said retaining means, each of said retaining means comprising an L-shaped member fixed to one of said halves, said member and said half forming a chamber receiving the laterally projecting portions on the barrel.

7. In a syringe according to claim 2 wherein said ridges are constructed of a material harder than the material of the radial projecting means on the plunger.

* * * * *